United States Patent [19]

Handy et al.

[11] 4,047,425
[45] Sept. 13, 1977

[54] TESTING DEVICE FOR MEASURING LATERAL PRESSURE INDUCED ON A MATERIAL BY A VERTICAL APPLIED PRESSURE

[75] Inventors: Richard L. Handy, Des Moines; James M. Hoover, Ames, both of Iowa

[73] Assignee: Iowa State University Research Foundation, Inc., Ames, Iowa

[21] Appl. No.: 641,545

[22] Filed: Dec. 17, 1975

[51] Int. Cl.² ............................................. G01N 3/08
[52] U.S. Cl. ....................................................... 73/94
[58] Field of Search ................... 73/88 E, 94, 388 R, 73/410, 84, 88 R; 100/99

[56] References Cited

U.S. PATENT DOCUMENTS 1,998,722  4/1935  Hveem ................................... 73/94

FOREIGN PATENT DOCUMENTS 862,376  6/1953  Germany .............................. 73/88 E Primary Examiner—Jerry W. Myracle
Attorney, Agent, or Firm—Zarley, McKee, Thomte & Voorhees

[57] ABSTRACT

A testing device for measuring a lateral pressure induced on a material by a vertical applied pressure, the testing device comprising in combination a material-holding receptacle which is capable of lateral expansion in response to a vertical applied force on a material contained in the receptacle, and a sensing means positioned on the receptacle to sense the amount of lateral expansion of the receptacle.

10 Claims, 5 Drawing Figures

TESTING DEVICE FOR MEASURING LATERAL PRESSURE INDUCED ON A MATERIAL BY A VERTICAL APPLIED PRESSURE

BACKGROUND OF THE INVENTION

The lateral pressure induced upon soil under a vertical applied pressure is an important and fundamental aspect of engineering behavior of the soil particularly in relationship to the pressure on retaining walls and to the soil-bearing capacity under loads. For example, assume that the lateral pressure for a particular soil equals one-half of the vertical pressure; then a vertical loading of 100 p.s.i. will cause a lateral pressure of 50 p.s.i. on an adjacent retaining wall, the ratio of lateral to vertical pressure in this case being one-half. Thus, the adjacent retaining wall must be able, as a minimum, to withstand a lateral pressure equal to one-half the vertical stress from the weight of the soil, which of course increases with depth. The relationship to bearing capacity of a given soil is somewhat more complicated than the above example since the lateral pressure tends to cause adjacent underlying soil to be displaced laterally which can induce a bearing capacity failure or what is termed "rutting." This is true because, when the adjacent soil is displaced laterally, soil adjacent to the laterally displaced soil develops its own minor principal stress as an uplift pressure that may exceed the restraining weight of the adjacent overburden soil.

As one can see, the importance of monitoring the ratio of lateral stress to vertical stress is of critical importance for placing any structure upon the soil. It is therefore of value of assess this relationship and to evaluate its effect for a given soil sample in order to known whether or not the soil can properly withstand the applied vertical pressure. The ratio of lateral to vertical stress is known as the Rankine stress ratio and is termed "K."

It is an object of this invention to provide a soil testing device which can continually monitor the Rankine stress ratio on a soil sample as vertical applied pressure is increased, in order to determine the lateral stresses induced by a given vertical applied pressure in adjacent soil.

An additional object of this invention is to provide a Rankine stress monitoring device which may be used either on undisturbed field samples or soil samples which have been subjected to pre-treatment in order to simulate anticipated environmental conditions.

Still another object of this invention is to provide a continuous K testing device which can be utilized to test soil having been subjected to all sorts of environmental conditions such as freezing, thawing, snow, water soaking, or other conditions.

Yet another object of this invention is to monitor the Rankine stress ratio during a program of cyclical loading and unloading designed to simulate soil stress conditions that are known to occur in soils as a result of vehicular traffic or earthquakes.

The manner and method of accomplishing the above identified objects as well as objects which will be hereinafter mentioned, will become apparent from the following detailed description of the invention.

BRIEF DESCRIPTION OF THE DRAWINGS

This invention consists in the construction, arrangements and combination of the various parts of the device, whereby the objects contemplated are attained as hereinafter more fully set forth, specifically pointed out in the claims, and illustrated in the accompanying drawings in which:

DETAILED DESCRIPTION OF THE INVENTION

Figure 1:
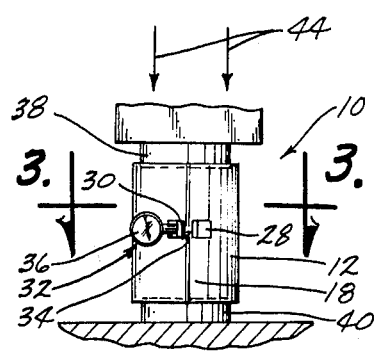
FIG. 1 is a side view of the testing device of this invention.
Figure 2:
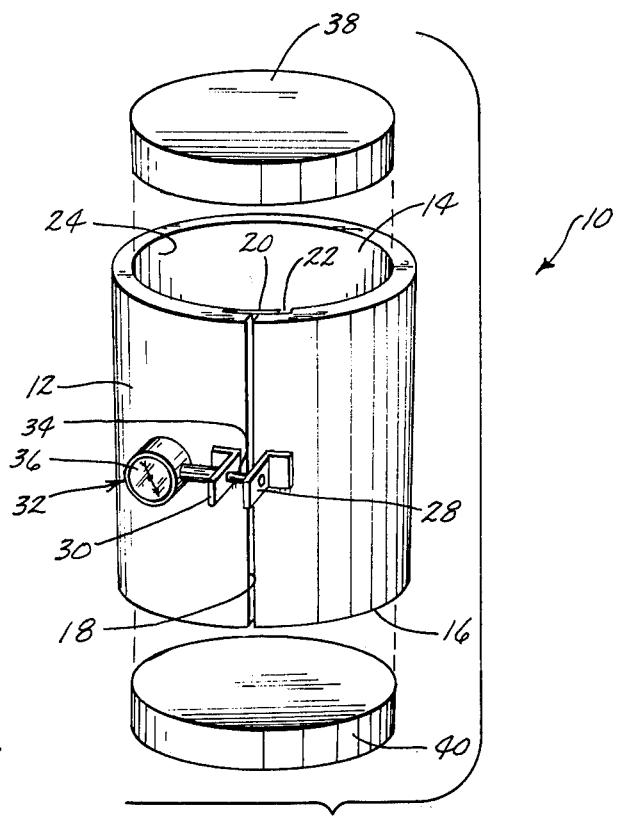
FIG. 2 is a perspective view of the testing device of this invention showing the relationship of the various components of the testing device.
Figure 3:
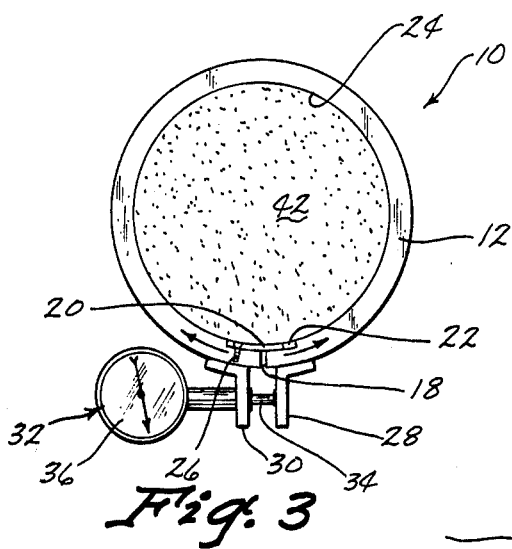
FIG. 3 is a plan view with the closure top removed.

The testing device of this invention, as distinguished from certain other testing devices, has the advantage of being able to test soil samples that have no cohesion since, in the device of this invention, the soil is confined wholly within the device thereby avoiding the need for cohesive samples.

The continuous Rankine stress monitoring device 10 is comprised of a main body portion cylindrical receptacle 12 having an open top end 14 and an open bottom end 16. Cylindrical receptacle 12 has a slit 18 along its entire length parallel to the longitudinal axis of cylindrical receptacle 12, which is sometimes hereinafter referred to as a cylindrical sleeve.

Positioned in abutting relationship to slit 18 within cylindrical receptacle 12 is a removable shield 20. Preferably, shield 20 is positioned in an inset 22 which extends along the inside wall surface 24 along the entire length of cylindrical receptacle 12 parallel to slit 18. Shield 20 is fastened only on one side by fastening means 26 to the inside wall surface 24 of cylindrical receptacle 12.

Support bracket 28 is mounted to cylindrical sleeve 12 adjacent to longitudinal slit 18 at about the midpoint of longitudinal slit 18. In like manner, support bracket 30 is positioned on the opposite side of slit 18 in abutting relationship to slit 18 and in opposing relationship to bracket 28.

Strain indicator 32 is mounted bracket 30 with its expansion stem 34 bearing against bracket 28. Stem 34 is slidably movable towards and away from strain indicator 32. Strain indicator 32 is of conventional construction and its constructional details with not therefore be specifically mentioned herein.

Cylindrical receptacle 12 has a top closure 38, and a bottom closure 40. Top closure 38 and bottom closure 40 correspond to the inside closed diameter of cylindrical receptacle 12. Closure members 38 and 40 are movable along the longitudinal axis of cylindrical receptacle 12.

In actual operation the continuous K testing device works as follows. A soil sample 42 is placed within cylindrical receptacle 12 with, of course, bottom closure member 40 in position. Top closure member 38 is placed within cylindrical sleeve 12 directly on top of soil sample 42. A predetermined vertical applied pressure, as indicated by arrows 44, is applied downwardly against top closure member 38 and correspondingly on soil sample 42. The vertical applied pressure in the direction of arrows 44 causes an induced lateral pressure on the soil sample 42 and correspondingly on the internal wall surface 24 of cylindrical sleeve 12. The induced lateral pressure cases expansion of sleeve 12 transverse to its longitudinal axis with the result being that the width of slit 18 is increased. As the width of slit 18 increases, removable shield 20, since it is only fastened on one side of slit 18, slides with respect to the inside wall surface 24 on the opposite side of slit 18 from fastening member 26. Soil sample 42 is prevented from falling through slit 18 by removable shield 20 which is preferably comprised of Teflon.

As slit 18 expands in response to the vertical applied pressure, expansion stem 34 of strain indicator 32 is spring-loaded towards bracket 28 across slit 18. Strain indicator dial 36 measures the distance expansion stem 34, moves and provides a reading thereon.

By application of a series of predetermined vertical pressures and monitoring of the corresponding developed lateral pressure through strain indicator dial 36 one obtains a continuous response record for a particular soil, such that the developed lateral pressure is predicted for any anticipated level of vertical pressure.

The cylindrical receptacle 12 is preferably comprised of cold rolled steel, with its elasticity being controlled by the wall thickness of cylindrical receptacle 12. Thus, cylindrical receptacle 12 behaves like a spring and is movable in response to the vertical applied pressure from a nonexpanded condition to an expanded condition in which the width of slit 18 is increased. The amount of expansion and corresponding increase in width in slit 18 depends on the internal expansion pressure. Readings on strain indicator dial 36 can be calibrated for given applied internal expansion pressure in the direction of arrows 44 in order to calibrate the instrument.

It desired, a linear motion transducer can be utilized in place of strain indicator 32.

A strain gauge can also be utilized in place of stress indicator 32 with the strain gauge recording the bending of receptacle 12.

Of course, as previously mentioned herein, the wall thickness of cylindrical receptacle 12 determines the lateral restraint to the vertical applied pressure for the soil being tested.

Figure 4:
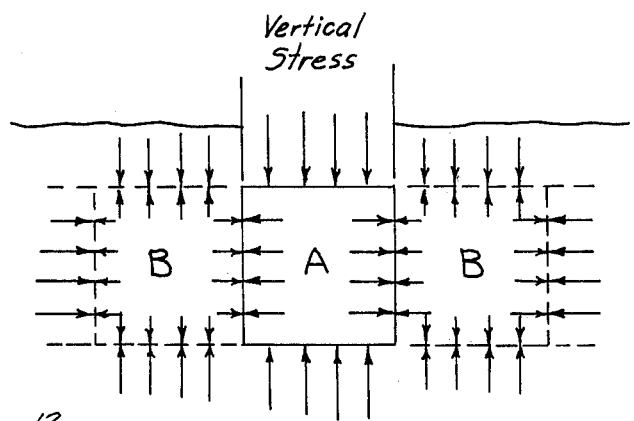
FIG. 4 is a schematic view showing the various stress components upon soil subjected in situ to a vertical load, which figure is representative of typical field loading situations.

In a field loading situation this intensity of lateral confinement varies depending on the soil, in accord with the stress diagram in FIG. 4 where square "A" represents the soil under test and squares "B" represent lateral confining soil. A measure of confining soil stiffness is its modulus of elasticity E, in p.s.i. For a realistic test the typical cylindrical receptacle 12 mold expansion modulus, as measured in p.s.i., is the following for various types of soil samples.

| Soil | Mold Expansion Modulus, psi |
|---|---|
| Dense gravel, sand-gravel, crushed rock, sand | 18,000 – 20,000 |
| Loose sand, dense silt, clay | 4,000 – 6,000 |
| Soft silt, clay | 1,500 – 2,500 |

The mold stiffness also may be selected to simulate elastic behavior of a confining structure, as a retaining wall. For special purposes, such as comparisons of many soil samples, a constant stiffness may be preferred even though this does not represent a best simulation of field stress conditions. It should be noted that even in this case, the elastic behavior of the K-test mold is much closer to field conditions than is presented by conventional soil shear strength testing wherein the confining pressure is maintained at an arbitrary constant level which bears little or no relationship to actual stresses occurring in the field.

If desired, the mold interior wall surface 24 can be polished and chromeplated to reduce friction and abrasion.

Figure 5:
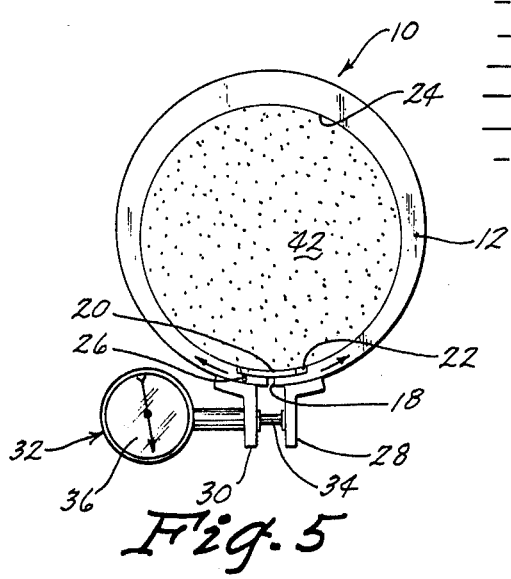
FIG. 5 is a view similar to FIG. 3 but of the embodiment employing a non-uniform thickness receptacle.

As shown in FIG. 5, in a preferred embodiment of the invention described herein the wall thickness of receptacle 12 directly behind slit 18 is increased to a predetermined thickness with the wall thickness progressively decreasing for portions of the wall closer to slit 18. As a result, the wall thickness is greatest at the point of the largest bending moment, and correspondingly the point of greatest stress. Such a mold employing the preferred variable thickness receptacle wall allows measurement of greater stresses than a uniform wall thickness receptacle.

Certian other advantages for the structure of this invention are apparent from the very fact that the test is a continuous test which measures developed stresses rather than current engineering practice which measure maximum values.

For example, most soils have both internal friction $\phi$ and a cohesion intercept $c$, or shearing strength under zero applied normal stress. Mathematically, it can be shown that from a consideration of the changes in the Rankine stress ratio, K, one may define by mathematical computation both cohesion $c$ and friction angle $\phi$ for an individual soil.

A particular advantage of the continuous K-test device is that it may be used with either undisturbed field samples or laboratory molded samples, and because of the confined nature of the test and mobility of the test mold practically any pre-treatment may be used which simulates an anticipated environment. This is in contrast to other tests where the lack of confinement may allow samples to fall apart. For example, K-test specimens may be saturated with water prior to testing. Not only does this impose an extreme environmental condition that frequently occurs in the field, valuable supplementary data may be obtained on expansive or collapsible character of the particular soil, by measuring the specimen height before and after soaking. A realistic surcharge load also may be used during soaking to better simulate field conditions. Simarily, specimens may be dried to indicate shrinkage, or they may be frozen and thawed to indicate deleterious frost action, or they may be chemically treated to improve stability. No other test offers these potentials in quite so convenient and controllable a form, because practically all tests which provide $c$, $\phi$ and K data require the use of several different specimens.

It can also be seen that an additional advantage of the structure of the K-test device of this invention is that the testing may be performed under slow or static loading conditions to give a behavior usually identified as soil creep. Alternatively, the test may be performed with a cyclical loading and unloading designed to simulate soil stress conditions that are known to occur in soils as a result of vehicular traffic or earthquakes.

As heretofore previously mentioned the directness of the soil test is an advantage compared with prior art tests since in use of the device of the present invention the developed k, $c$ $\phi$ and $\epsilon$, unit strain are evaluated rather than the maximum or limiting values.

In current engineering practice, maxima are obtained and divided by an arbitrary number called a "factor of safety" to assure that the failure stress conditions are never reached. Since the limiting conditions are seldom reached simultaneously through a soil mass, most soil mechanics problems are theoretically indeterminate, i.e., the number of unknowns exceeds the number of variables and critical assumptions must be made for the analysis. These are all covered in the factor of safety. This is to be contrasted with the analysis which can be made utilizing the structure of the present invention wherein the design allows the acutal measurement of a developed response rather than a determination of maximum responses. It is therefore much closer to actual environmental conditions.

Thus as can be seen, the structure and method of the present invention have many advantages and accomplish all of the stated objects of the invention.

What is claimed is:

1. A testing device to measure the lateral pressure induced on a material by a vertical applied pressure, said testing device comprising in combination,
    a material holding receptacle which is capable of lateral expansion in response to a vertical applied force on a material contained in said receptacle, and
    a sensing means positioned on said receptacle to sense the amount of lateral expansion of said receptacle,
    said cylindrical sleeve having a slit along its entire length parallel to the longitudinal axis of said sleeve.

2. The testing device of claim 1 wherein said receptacle is an elastic, cylindrical sleeve.

3. The testing device of claim 2 wherein said cylindrical sleeve has top and bottom closure members, said closure members being movable along the longitudinal axis of said cylinder whereby said applied pressure may be varied.

4. A testing device to measure the lateral pressure induced on a material by a vertical applied pressure, said testing device comprising in combination,
    a material holding receptacle which is capable of lateral expansion in response to a vertical applied force on a material contained in said receptacle, and
    a sensing means positioned on said receptacle to sense the amount of lateral expansion of said receptacle,
    said receptacle being an elastic, cylindrical sleeve, said cylindrical sleeve having top and bottom closure members, said closure members being movable along the longitudinal axis of said cylinder whereby said applied pressure may be varied,
    said cylindrical sleeve having a slit along its entire length parallel to the longitudinal axis of said sleeve.

5. The testing device of claim 4 wherein a removable shield is positioned within said sleeve in abutting relationship to said slit.

6. The testing device of claim 5 wherein said sensing means is a strain indicator from which internal pressure on said cylindrical sleeve may be calculated.

7. The testing device of claim 6 wherein said strain indicator is attached to said sleeve across said slit.

8. The testing device of claim 7 wherein said strain indicator is mounted on said sleeve on one side of said slit and also mounted to said sleeve on the other side of said slit whereby said indicator is responsive to changes in the width of said slit.

9. The testing device of claim 4 wherein said cylindrical sleeve is comprised of a variable wall thickness material with the portion of said wall opposite said slit being the thickest portion of said wall.

10. The testing device of claim 9 wherein said wall thickness is greatest at the point of largest bending moment and progessively decreases for wall portions closer to said longitudinal slit.

* * * * *